United States Patent
Oron et al.

(10) Patent No.: US 7,079,955 B2
(45) Date of Patent: Jul. 18, 2006

(54) SYSTEM AND METHOD FOR INTEGRATED ANALYSIS OF DATA FOR CHARACTERIZING CARBOHYDRATE POLYMERS

(75) Inventors: Assaf Peretz Oron, Seattle, WA (US); Einat Or, Tel Aviv (IL); Ofer Markman, Rehovot (IL); Leonid Shvartser, Lod (IL); Nava Zaarur, Moshav Givaati (IL)

(73) Assignee: Procognia, Ltd., Ashdod (IL)

( * ) Notice: Subject to any disclaimer, the term of this patent is extended or adjusted under 35 U.S.C. 154(b) by 243 days.

(21) Appl. No.: 10/415,955

(22) PCT Filed: Nov. 5, 2001

(86) PCT No.: PCT/US01/47084

§ 371 (c)(1),
(2), (4) Date: Mar. 22, 2004

(87) PCT Pub. No.: WO02/44714

PCT Pub. Date: Nov. 5, 2001

(65) Prior Publication Data

US 2004/0153252 A1  Aug. 5, 2004

Related U.S. Application Data

(60) Provisional application No. 60/246,006, filed on Nov. 3, 2000, provisional application No. 60/246,009, filed on Nov. 3, 2000, provisional application No. 60/245,887, filed on Nov. 3, 2000, provisional application No. 60/245,817, filed on Nov. 3, 2000.

(51) Int. Cl.
*G06F 19/00* (2006.01)

(52) U.S. Cl. ........................................ 702/20; 435/174

(58) Field of Classification Search ................ 702/20, 702/22, 27, 28, 30, 182–185; 436/145, 164–165, 436/174–175
See application file for complete search history.

(56) References Cited

U.S. PATENT DOCUMENTS

2004/0229382 A1* 11/2004 Breaker et al. ............. 436/531

FOREIGN PATENT DOCUMENTS

WO   WO 95/31177   11/1995

(Continued)

OTHER PUBLICATIONS

Chemical Abstracts 105(19) (1986): "Preparation of oligosaccharides by gel filtration chromatography" Shengwu Huaxue Zazhi 2(3): 69-74 (Abstract only).

(Continued)

*Primary Examiner*—Edward Raymond
(74) *Attorney, Agent, or Firm*—Ivor R. Elrifi; David E. Johnson; Mintz Levin

(57) ABSTRACT

A system and method for characterizing carbohydrate polymers according to maps obtained from experimental data. Preferably, the data is obtained from a plurality of different types of experimental assays for characterizing the carbohydrate polymer. More preferably, at least one such assay involves binding a saccharide-binding agent to the carbohydrate polymer. One or more features of the carbohydrate polymer are then preferably characterized. These features are preferably derived from maps of the data obtained from assays involving the sample carbohydrate polymer. These maps are more preferably analyzed at a plurality of levels, with each level providing more abstract biological information. Most preferably, new types of experimental data are introduced to the process of analysis at each level, in order to support more complex analyses of the data. Optionally and most preferably, maps are eliminated at each level as being inconsistent with the experimental data. New maps are most preferably added at a higher level only if they are derived from the new experimental data which has been introduced at that level, in order to prevent a combinatorial explosion at successive levels of data analysis.

29 Claims, 8 Drawing Sheets

FOREIGN PATENT DOCUMENTS

| | | |
|---|---|---|
| WO | WO 99/31267 | 6/1999 |
| WO | WO 00/68688 | 11/2000 |
| WO | WO 01/84147 | 11/2001 |
| WO | WO 02/37106 | 5/2002 |

OTHER PUBLICATIONS

Chemical Abstracts 117(11) (1992): "The multiple attack of endo-1,3-beta-gluconase L-IV from the marine mollusk *Spisula sachalinesis* III. Evolution of the total distribution of laminarin hydrolysis products by glucanase L-IV and L0." Biokhimya 57(2): 275-8 (Abstract only).

Lepagnol-Descamps et al., (1998) "Purification and determination of the action pattern of *Haliotis tuberculata* laminarinase". Carbohydrate Research 310(4):283-9.

Alban, et al. (1992) "Synthesis of laminarin sulfates with anticoagulant activity". Arzneimittel Forschung. Drug Research 42(8):1005-8.

* cited by examiner

SYSTEM AND METHOD FOR INTEGRATED ANALYSIS OF DATA FOR CHARACTERIZING CARBOHYDRATE POLYMERS

This application is a 371 of PCT/US01/47084 filed Nov. 5, 2001 which claims benefit of U.S. provisional application 60/246,006 filed Nov. 3, 2000 which claims benefit of U.S. provisional application 60/246,009 filed Nov. 3, 2000 which claims benefit of U.S. provisional application 60/245,887 filed Nov. 3, 2000 which claims benefit of U.S. provisional application 60/245,817 Nov. 3, 2000.

FIELD OF THE INVENTION

The present invention is of a system and method for integrated analysis of data for characterizing carbohydrate polymers, and in particular, is of such a system and method in which the data is obtained from a plurality of different types of experimental assays for characterizing the carbohydrate polymer.

BACKGROUND OF THE INVENTION

Oligosaccharides and polysaccharides are polymers that consist of monosaccharide (sugar) units that are connected to each other via glycosidic bonds. These polymers have a three-dimensional structure, in addition to the linear (two-dimensional) structure of the sequence of monosaccharide units. Furthermore, recent studies have shown that these carbohydrate polymers also carry biological information. For example, certain proteins and glycoproteins, or proteins that also feature carbohydrate moieties, have been shown to have binding specificity for certain types of carbohydrate polymers. These proteins and glycoproteins are called "lectins", and their role in various biological and pathological processes is only beginning to be elucidated. Originally, the term "lectins" referred to proteins isolated from plants that bind saccharides. For the purpose of this application, the term "lectin" also encompasses saccharide-binding proteins from animal species (e.g. "mammalian lectins"). Thus, carbohydrate polymers, like DNA or proteins, clearly have an important biological function which should be studied in greater detail.

The saccharide chain of the carbohydrate polymer has, like a chain of DNA or protein, two dissimilar ends. In the case of saccharide chains, these are the reducing end (corresponding to the aldehyde group of the linear sugar molecule) and the non-reducing end. Unlike proteins and DNA, however, saccharides may also be branched, with essentially each of the sugar units in the saccharide serving as an optional branching point. Thus, the three-dimensional structure of the carbohydrate polymer is clearly highly complex with regard to the biological function of the saccharide chain, since even the two-dimensional structure is more complex because of the presence of branches in the chain.

As previously described, there are a number of proteins that bind to saccharides, one example of which is the lectins. Many of these proteins bind specifically to a certain short oligosaccharide sequence. Antibodies are proteins that specifically recognize certain molecular structures. Antibodies may also recognize saccharide structures, as do lectins. Glycosidases are enzymes that cleave glycosidic bonds within the saccharide chain. Also glycosidases may recognize certain oligosaccharide sequences specifically. Glycosyltransferases are enzymes that cleave the saccharide chain, but further transfer a sugar unit to one of the newly created ends.

The art of structural determination of polysaccharides has not developed as rapidly as the art of protein analysis and DNA analysis. Furthermore, the analysis of a very important part of most mammalian proteins, i.e. of their attached saccharides and glycans, has been generally slower compared to the advance made in DNA and protein analysis technology.

Advanced analysis methods have been introduced in the fields of protein and DNA sequencing a number of years ago. However, the development of such methods and techniques are aided by the fact that the components that make up DNA and proteins are connected to each other by only one kind of connection (the 5' to 3' phosphoric acid bridge in DNA, and the peptide bond in proteins). DNA contains only four different components (the nucleic acids), while proteins contain about 20 different components (the amino acids). Although modified amino acids exist, a protein must first be synthesized, according to the genetic code, by using a DNA template. Therefore, the number and kind of amino acids that exist in a newly synthesized protein is restricted to the limited repertoire of amino acids represented in the genetic code. This code is universal, with only minor differences, for all life forms.

For the above structural reasons, the structural analysis of proteins and of DNA is today a simple, rapid, and relatively inexpensive procedure that does not require highly skilled personnel.

In contrast, a multitude of methods for the analysis of saccharide structures have been developed, each with its own shortcomings. It is today not possible, independent of the degree of sophistication of the method used, to determine the entire sequence of a polysaccharide or even of an oligosaccharide by using a single technique. There are several reasons for this difficulty. First, saccharides are synthesized template-independent. In the absence of structural information, the researcher must therefore assume that the building units are selected from any of the saccharide units known today. In addition, these units may have been modified, e.g. by the addition of sulfate groups, during synthesis.

Second, the connections between saccharide units are multifold. A saccharide may be connected to any of the C1, C2, C3, C4, or C6 atom if the sugar unit it is connected to is a hexose. Moreover, the connection to the C1 atom maybe in either α or β configuration.

Thirdly, saccharides may be branched, which further complicates their structure and the number of possible structures that have an identical number and kind of sugar units.

A fourth difficulty is presented by the fact that the difference in structure between many sugars is minute, as a sugar unit may differ from another merely by the position of the hydroxyl groups (epimers).

A method for characterizing carbohydrate polymers is disclosed in PCT Application No. PCT/IL00/00256, which is hereby incorporated by reference as if fully set forth herein. According to this method, one or more saccharide-binding agents are attached to a surface. These agents may optionally be lectins, antibodies, other types of proteins that bind to saccharides, or polysaccharide-cleaving or modifying enzymes, for example. Next, the carbohydrate polymer of interest is incubated with the saccharide-binding agents on the surface. Such a carbohydrate polymer may be any molecule with a polysaccharide component, such as a polysaccharide itself, a glycoprotein or a glycolipid for example. If the carbohydrate polymer binds to the saccharide-binding agent, then a complex is formed. This complex may then be detected with a second saccharide-binding agent, which for example may optionally have some type of attached label for the purpose of detection. Examples of such a label include but are not limited to a chromogenic label, a radiolabel, a fluorescent label, and a biotinylated label.

The use of a plurality of such saccharide-binding agents, whether fixed to the substrate and/or employed as the second (soluble) saccharide-binding agent, characterizes the carbohydrate polymer of interest by providing a "fingerprint" of the saccharide. Such a fingerprint can then be analyzed in order to obtain more information about the carbohydrate polymer. Unfortunately, the process of characterization and interpretation of the data for carbohydrate polymer fingerprints is far more complex than for other biological polymers, such as DNA for example. Unlike binding DNA probes to a sample of DNA for the purpose of characterization, the carbohydrate polymer fingerprint is not necessarily a direct indication of the components of the carbohydrate polymer itself. DNA probe binding provides relatively direct information about the sequence of the DNA sample itself, since under the proper conditions, recognition and binding of a probe to DNA is a fairly straightforward process. Thus, a DNA "fingerprint" which is obtained from probe binding can yield direct information about the actual sequence of DNA in the sample.

By contrast, binding of agents to carbohydrate polymers is not nearly so straightforward. As previously described, even the two-dimensional structure (sequence) of carbohydrate polymers is more complex than that of DNA, since carbohydrate polymers can be branched. These branches clearly affect the three-dimensional structure of the polymer, and hence the structure of the recognition site for the binding agent. In addition, recognition of binding epitopes on carbohydrate polymers by the binding agents may be affected by the "neighborhood" of the portion of the molecule that is surrounding the epitope. Thus, the analysis of such "fingerprint" data for the binding of agents to the carbohydrate polymer of interest is clearly more difficult than for DNA probe binding, for example.

In addition, the analysis is further complicated by the possibility of a combinatorial explosion, which can result when attempting to search through a combinatorial space. A combinatorial space is defined as having multiple combinations of basic elements. These combinations may differ according to the values of different types of these elements, the structure of the resultant combination of elements, or may be produced as a result of both factors. Combinatorial spaces often occur in biology, as many elementary biological materials are themselves produced through combinations of relatively basic building blocks, yet are highly complex in their resultant structure and/or function. Attempts to analyze fingerprint data from carbohydrate polymers, as described above, is one example of a combinatorial space. A search through such a combinatorial space may also be termed a "combinatorial search".

Searching through combinatorial space is a difficult problem, since the despite the apparent simplicity of these different types of building blocks, the huge number and complexity of the resultant combinations make an exhaustive search of the combinatorial space difficult if not impossible. Thus, searching through these types of combinatorial spaces, particularly for biological problems, has typically proved to be resistant to modeling and prediction by computational algorithms in software programs.

SUMMARY OF THE INVENTION

The background art does not teach or suggest a method for rapidly and/or automatically analyzing data from a plurality of assays involving the carbohydrate polymer of interest. The background art does not teach or suggest such a method for data analysis from fingerprint assays. In addition, the background art does not teach or suggest combining fingerprint data with data from other types of experimental assays, in order to find and analyze patterns in the data. The background art also does not teach or suggest the management and organization of such data.

The present invention discloses a system and method for characterizing carbohydrate polymers according to patterns obtained from experimental data. Preferably, the data is obtained from a plurality of different types of experimental assays for characterizing the carbohydrate polymer. More preferably, at least one such assay involves binding a saccharide-binding agent to the carbohydrate polymer in order to obtain a fingerprint. One or more features of the carbohydrate polymer are then preferably characterized.

Hereinafter, the term "glycomolecule" includes any molecule with a polysaccharide component. Examples include polysaccharide, a glycoprotein, and glycolipid.

Hereinafter, the term "saccharide-binding agent" refers to any entity which is capable of binding to a saccharide, whether monosaccharide, oligosaccharide, polysaccharide or a combination thereof, including but not limited to, a lectin, an antibody, another protein which binds to or otherwise recognizes a saccharide, and a polysaccharide-cleaving or modifying enzyme.

Hereinafter, the term "carbohydrate polymer" refers to any polysaccharide or oligosaccharide, or other structure containing a plurality of connected monosaccharide units.

Hereinafter, the term "sample carbohydrate polymer" refers to the carbohydrate polymer under test, for which experimental data is derived for the purposes of further analysis.

Hereinafter, the term "comparison carbohydrate polymer" refers to the carbohydrate polymer for which data is obtained for comparison to the sample carbohydrate polymer. The comparison carbohydrate polymer may optionally be a standard known carbohydrate polymer, for which the structure is known.

Hereinafter, the term "computational device" includes any type of computer or any device capable of performing computations and/or which have an operating system, including but not limited to enhanced cellular telephones such as WAP-enabled cellular telephones, wearable computers of any sort.

For the present invention, a software application could be written in substantially any suitable programming language, which could easily be selected by one of ordinary skill in the art. The programming language chosen should be compatible with the computational device according to which the software application is executed. Examples of suitable programming languages include, but are not limited to, C, C++ and Java.

In addition, the present invention could be implemented as software, firmware or hardware, or as a combination thereof. For any of these implementations, the functional stages performed by the method could be described as a plurality of instructions performed by a data processor.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
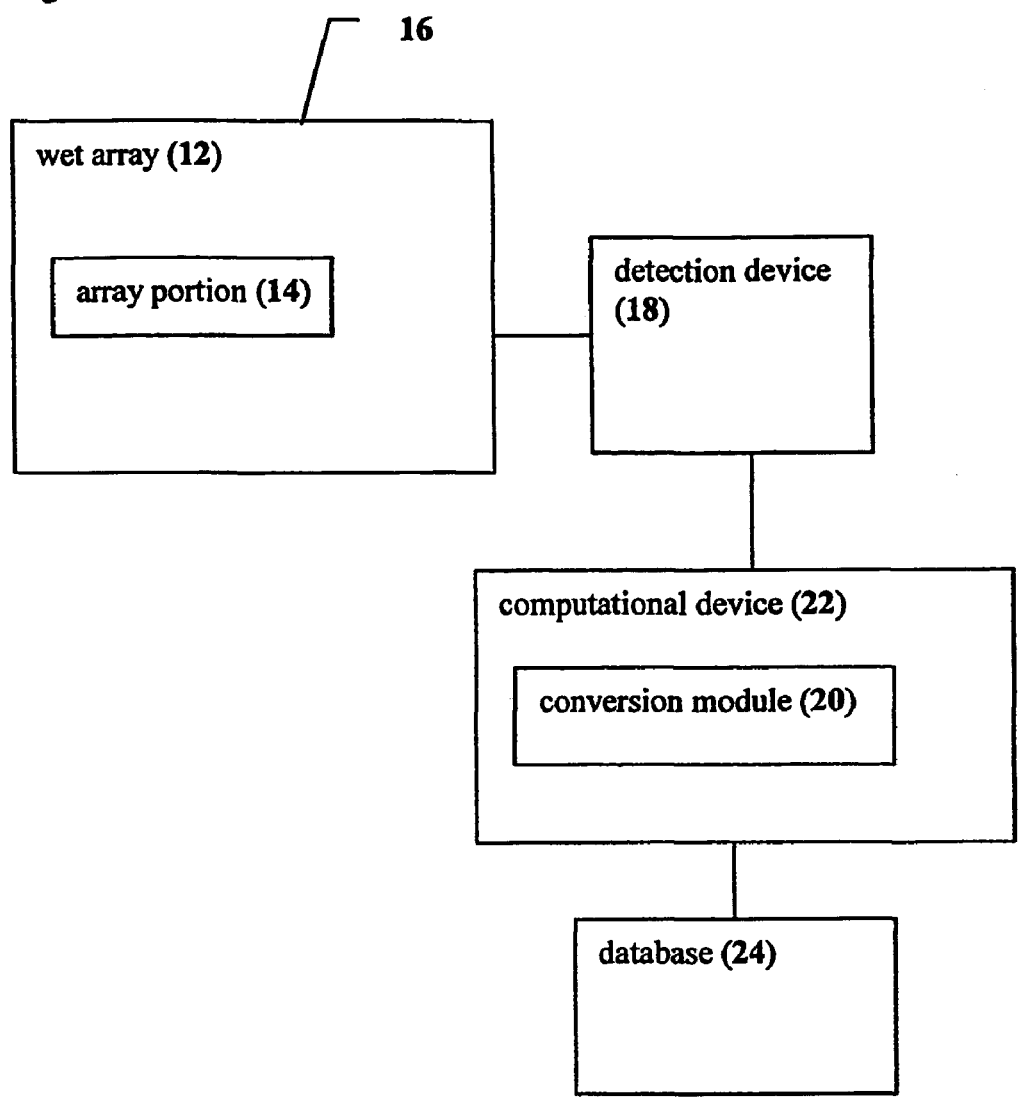
FIG. 1 shows a schematic block diagram of an exemplary experimental system for obtaining the raw data for determining a fingerprint for a carbohydrate polymer of interest for the present invention.

The present invention discloses a system and method for characterizing carbohydrate polymers according to maps obtained from experimental data. Preferably, the data is obtained from a plurality of different types of experimental assays for characterizing the carbohydrate polymer. More preferably, at least one such assay involves binding a saccharide-binding agent to the carbohydrate polymer. The map of binding by a plurality of agents is then analyzed in order to at least partially characterize the carbohydrate polymer. The map of binding is used to form a fingerprint, which also incorporates data from other types of assays, for at least a partial characterization of one or more features of the carbohydrate polymer.

These features are preferably derived from maps of the data obtained from assays involving the sample carbohydrate polymer. These maps are more preferably analyzed at a plurality of levels, with each level providing more abstract biological information. Most preferably, new types of experimental data are introduced to the process of analysis at each level, in order to support more complex analyses of the data. Optionally and most preferably, maps are eliminated at each level as being inconsistent with the experimental data. New maps are most preferably added at a higher level only if they are derived from the new experimental data which has been introduced at that level, in order to prevent a combinatorial explosion at successive levels of data analysis.

One non-limiting example of a type of assay which is suitable for use with the present invention is the fingerprint assay, in which saccharide-binding agents are incubated with a carbohydrate polymer of interest At a basic level, the analyzed binding data is used to determine a fingerprint for the carbohydrate polymer. This fingerprint is actually a numeric representation of the detection of the presence of binding by the saccharide-binding agents to the carbohydrate polymer. The fingerprint itself thus characterizes the carbohydrate polymer at some level.

Next, the fingerprint is optionally internally analyzed in order to obtain various possible maps which fit the experimental data. For example, certain maps of lectin binding, particularly with sets of model saccharide-binding agents, may be indicative of the presence of a particular type or class of the carbohydrate polymer. Another such map may indicate the presence of a false negative or "hole", for a lectin or other saccharide-binding agent which should have bound at a particular location, but which did not in fact bind. The presence of a false negative may indicate the presence of a particular type of saccharide "neighborhood", which affects the binding of the saccharide-binding agent, such that even if a particular sequence is present, binding of the agent itself to the sequence is blocked.

At this level of analysis, optionally many different, mutually contradictory maps may be considered. Preferably, the cut-off or probabilistic threshold for these maps is low, in order to permit as many maps as possible to be considered. These maps are then preferably examined and optionally eliminated in subsequent levels of analysis, as described in greater detail below.

At the next level of analysis, preferably information from other types of assays is incorporated. These assays are optionally and preferably performed with the same or similar experimental material as for the fingerprint data, in order to reduce or even eliminate experimental artifacts. In addition, the use of at least similar experimental material enables results for the sample carbohydrate polymer to be compared to standard, known carbohydrate polymers, without requiring absolute accuracy of the experimental assay, but only reproducibility. For example, the assay could optionally include the use of glycosidases, elimination of reducing ends, and other modifications of the sample carbohydrate polymer. More preferably, previously obtained maps are eliminated at this level as being inconsistent with the experimental data.

The next level preferably enables data to be incorporated from external databases, such that optionally data is used from different experimental materials. Such information could be related to the composition of the saccharide, its source, and possibly other information as well. For example this information could include whether the sample carbohydrate is part of a glycoprotein, the use of other types of carbohydrate binding agents such as cytokines, and so forth. For example, if maps of data obtained from previous stages are definitely incompatible with the source or the composition of the saccharide, then they should be eliminated. The introduction of such data is preferably performed at least partially with information from known carbohydrate-polymers. For example, an unknown saccharide could be classified as "EPO-like", which could help to guide future experiments.

As further level of analysis, the maps of data should be transformed, such that any reference to the original raw data is eliminated. Such a transformation is preferably performed by locating features of interest within the sample carbohydrate polymer. These features of interest may optionally be short sequences or portions of sequences of monosaccharides within the larger polymer sequence. A very simple example of such a feature is a glycosidase recognition site. Such features may also optionally be described as "sequence-based" features, in that they are characterized by at least a portion of the sequence of the carbohydrate polymer. Such features have the disadvantage of requiring absolute accuracy of the experimental data, rather than mere reproducibility. However, they have the advantage of being comparable over a wide variety of different known carbohydrate polymers, through data obtained from external databases as previously described.

Alternatively and/or additionally and preferably, these features of interest concern functional epitopes and/or sequence-based epitopes having a biological function of interest. By "functional" epitope, it is meant that at least a portion of the carbohydrate polymer appears to be associated with a particular function and/or type of function, regardless of the actual sequence of the carbohydrate polymer. Such a functional epitope may optionally be located through the performance of the same assay on a plurality of carbohydrate polymers, with only the requirement of reproducibility, rather than absolute accuracy. Of course, the functional epitope may also optionally be characterized by a sequence, such that the same epitope may optionally be both a sequence-based epitope and a functional epitope.

Also alternatively and/or additionally and preferably, these features of interest concern "characterization" features. These features are not necessarily discrete portions of the carbohydrate polymer, but rather are indicative of the classification, function or nature of the overall polymer, or some combination thereof. For example, such a characterization feature may enable the carbohydrate polymer to be determined to be "EPO-like". This determination would not necessarily immediately result in the location of specific functional epitopes within the polymer, for example, but may provide an indication that the carbohydrate polymer should be further examined for the possibility of such functional epitopes being present.

With regard to the non-limiting example of fingerprint data, as previously described with regard to PCT Application No. PCT/IL00/00256, which was previously incorporated by reference as if fully set forth herein, the raw binding data is obtained by detecting the presence of a labeled saccharide-binding agent which is bound to a complex formed between the carbohydrate polymer of interest and an immobilized saccharide-binding agent, which is itself bound to a fixed substrate. The label may optionally be a chromogenic label, a radiolabel, a fluorescent label, or a biotinylated label, for example. Regardless of the type of label, the raw data can optionally be obtained in the form of a binary (positive/negative) result, or alternatively may be in the form of a semi-quantitative result. Either type of result can then be converted to a numeric value, which would form part of the fingerprint for the carbohydrate polymer of interest. Thus, at the very least, the fingerprint according to the present invention would feature a string of numeric values, representing the results of the experimental binding assays.

According to preferred embodiments of the present invention, the values for the fingerprint are modified according to information obtained from the assay itself and/or the analysis of the raw data. For example, artifacts caused by the experimental system itself could optionally be removed, or their effect could be minimized. For example, false positive and/or negative results, problems caused by the system for detecting the presence of the label, and problems inherent in the use of any particular label should all preferably be considered in the determination of the numeric values for the fingerprint. In addition, with regard to the analysis of the signal itself, such issues as removing any background noise, and determining the proper threshold beyond which a signal indicates a true positive, are also important for the modification of the fingerprint to reflect the actual experimental conditions.

More preferably, the raw data is transformed in order to yield quantitative data. Quantitative data is particularly preferred if the carbohydrate polymer is manipulated by partial cleavage with glycosidases, such that a mixture of products from this reaction is expected (uncleaved, fully cleaved and partially cleaved). The use of quantitative data would clearly provide an advantage for the analysis of such a mixture of products, which in turn would alter the composition of the fingerprint.

According to further preferred embodiments of the present invention, regardless of the type of numeric value for the fingerprint (binary or semi-quantitative/quantitative), the two fingerprints could simply be compared according to a similarity score, with a positive score for identical results at each point in the array, and a penalty for different results. If each fingerprint has a large number of different elements, and/or if a search for similar fingerprints is to be performed in a database of a large number of fingerprints, optionally and more preferably, each fingerprint is treated as an address in a large, multi-dimensional array.

A more complex version of this method would not require data to have a binary value (identical/not identical), but would permit the likelihood of a signal being positive or negative to also be incorporated, as long any such likelihood can be first defined and then quantified.

The advantages of using direct comparisons between fingerprints of different carbohydrate polymers are that such comparisons only require the experimental evidence to be reproducible, but do not require accuracy in binding of saccharide-binding agents. Such tolerance of the data, and hence of the resultant method for fingerprint comparison, for vagaries of the experimental procedure and of the actual biology of the polymers, is a clear advantage of the method of the present invention.

The principles and operation of the present invention may be better understood with reference to the drawings and the accompanying description. Please note that the description provided with reference to the drawings is divided into four sections. The first section concerns the system and method for obtaining and managing the raw fingerprint data, as a non-limiting example of a type of experimental data which may be obtained according to the present invention; the second section concerns analysis of the fingerprint data to characterize the carbohydrate polymer; and the third section concerns the analysis of information from multiple sources of experimental data.

Section 1: Acquisition, Processing and Management of Fingerprint Data

Referring now to the drawings, FIG. 1 is a schematic block diagram of an exemplary experimental system for obtaining the raw data for determining a fingerprint for a carbohydrate polymer of interest. As shown, a system 10 features a wet array 12, in which the actual assay is performed with a plurality of immobilized saccharide-binding agents. Each such immobilized agent is located at a predetermined array portion 14, which is a predetermined location on a substrate 16. Preferably, each array portion 14 features a different immobilized saccharide-binding agent. The plurality of array portions 14 which is shown composes the entirety of wet array 12. Thus, each array portion 14 is an address on wet array 12; the data obtained from this address forms a part of the fingerprint for the carbohydrate polymer of interest, as described in greater detail below.

The carbohydrate polymer is then incubated with wet array 12, under conditions which permit specific binding of the carbohydrate polymer to one or more immobilized saccharide-binding agents. Such specific binding should result in the formation of a complex between the carbohydrate polymer and the immobilized saccharide-binding agent at a particular array portion 14.

The presence of the complex is then detected by incubating a second, solubilized saccharide-binding agent with wet array 12. The second solubilized agent features a label for detection. Therefore, if the solubilized agent binds to the complex at any particular array portion 14, the presence of such a complex can be detected by detecting the label. A detection device 18 is then used to detect the presence of the label, such that the selection of any particular detection device 18 depends upon the nature of the label. For example, a chromogenic label, such as a dye which becomes excited and fluoresces, can optionally be detected with a camera or other imaging device for detection device 18. Detection device 18 should be able to distinguish between signals from the label from each array portion 14.

Once the signal from each array portion 14 has been collected by detection device 18 and converted to electronic (digital) data, the resultant raw data is preferably transformed to a numeric value for the fingerprint, such that a numeric value for each address of the fingerprint corresponds to an address for wet array 12. The process of transformation is optionally and preferably performed by a conversion module 20, which may be optionally implemented as a software module for operation by a computational device 22. The fingerprint data is then preferably stored in a database 24 which is more preferably also controlled by computational device 22. Of course, a distributed implementation across a network of computational devices is also possible within the scope of the present invention (not shown).

According to preferred embodiments of the present invention, database 24 is implemented as follows. The wet process provides output files in various forms, for example from conversion module 20 as previously described. For example, these files may optionally be scanner output files of biochips and gels, and/or output files of laboratory devices such as detection device 18 for example. The scanner and/or laboratory device file may optionally be in the "TIFF" format for example. This data is then preferably stored as raw data in an experimental database (not shown). Preliminary processing is preferably performed on the output file of the laboratory device with the use of suitable software such as conversion module 20 for example. The output of the algorithm is then preferably stored in a standard relational database system (RDBMS) such as Oracle 8i DB server (Oracle Corp, Redwood Shores, Calif., USA) preferably by using a unique database schema, which has been adapted to the particular experimental and information management requirements of the experimental data. A database schema is standard for construction of a relational database, which is a collection of tables, with links between them. The graphical representation of the tables and the links is the schema.

In addition to the results, information about the experimental process (time, performer, materials involved etc.) is also preferably stored in the database. This output can be preferably then queried using many different criteria by any standard query tool. Examples of such criteria for characterizing experiments include, but are not limited to, use of a specified sample, performance by a specified researcher, performance between certain dates, obtaining results with a standard deviation larger than a particular percentage. Any information that is stored can also be criteria for searching through the database. The simplicity of the database structure enables the biologists to query the experiment results easily and efficiently, since there are many graphical query tools that enable even less computationally skilled employees to construct a query without knowing any programming language. These tools are available for relational databases.

Figure 2:
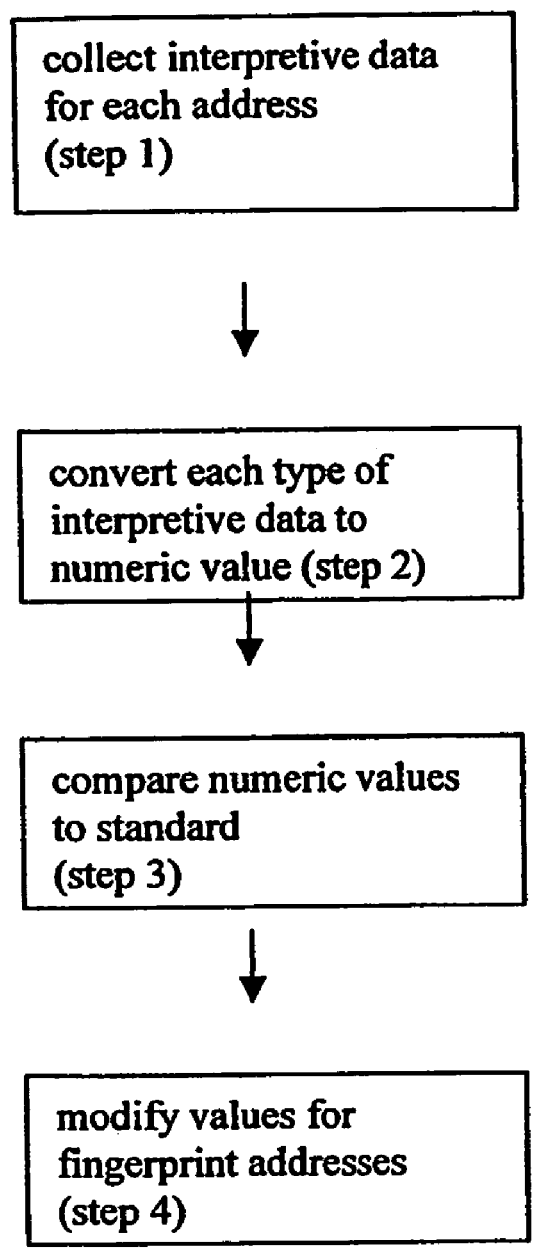
FIG. 2 is a flowchart of an exemplary method according to the present invention for modifying the fingerprint of the sample carbohydrate polymer according to information obtained from the experimental assay.

According to preferred embodiments of the present invention, the fingerprint is preferably adjusted according to information obtained from the assay itself. Such an adjustment is performed by filtering the values of the fingerprint according to interpretive information obtained from the assay itself. More preferably, probabilistic filtering is performed, such that the significance of the information and the likely effect on the values for the fingerprint are also considered. Such a filtering mechanism could optionally include a weighting function, for example, in order to determine the relative weight of the interpretive information. An example of a method for probabilistic filtering of the fingerprint data according to information obtained from the assay itself is described with regard to the method of FIG. 2.

As shown in stage 1, the interpretive data for each address of the fingerprint is collected. For example, such information may have optionally been separated into a plurality of different types of records for storage in a database. Therefore, stage 1 optionally includes the stage of searching through a database in order to retrieve information related to each such fingerprint address. The same information may optionally be of interest to more than one such fingerprint address.

In stage 2, each type of interpretive data is preferably converted to a numeric value and/or to a function. An example of conversion to a numeric value would be for the value of the threshold above which a signal obtained from the wet array of FIG. 1 is considered to be positive; that is, to indicate specific, positive binding of the saccharide-binding agent. Assuming that the value for the raw data for the address of the fingerprint is available, then the threshold value could be converted to a numeric value for later comparison in stage 3 below.

An example of a conversion to a function is for stringency conditions for permitting the solubilized saccharide-binding agent to bind to the complex of the carbohydrate polymer and the immobilized saccharide-binding agent on the substrate. Such conditions could also optionally be converted to a numeric value, which would then be applied for as a proportional factor against the numeric values of the fingerprint in stage 4 below. However, preferably the stringency conditions are used to create a function, in which the relative weights of different aspects of the conditions are used to scale the numeric values of the fingerprint in stage 4 below.

In stage 3, each type of numeric interpretive data is optionally and preferably compared against a standard for determining if the data should be used to alter the numeric value for the addresses of the fingerprint in stage 4 below. Alternatively, the numeric interpretive data could itself be weighted according to a weighting function, in order to the determine the probabilistic significance of the data, and the correct effect of the data on the values for the fingerprint during the process of filtering these values.

In stage 4, preferably the actual numeric values for the fingerprint addresses are filtered according to the interpretive data. The filtration process is more preferably a probabilistic process, in which the likely significance of the data is also considered. For interpretive data which is a function, the function is preferably applied to the numeric value of the fingerprint address, optionally using other numeric values of the interpretive data as parameters. For example, a weighting function could optionally be applied to each numeric value of the fingerprint address, in order to adjust the value. Alternatively, another such function would filter the values of the fingerprint by eliminating those values which are below or above a certain "cut-off" threshold, for example in order to adjust the minimum threshold for determining a particular signal of a sample in the fingerprint assay to be positive or negative.

For numerical interpretive data, preferably a predetermined function is used to determine the effect of the data on the numeric value of the address of the fingerprint. For example, the numerical interpretive data could optionally be subtracted from the numeric value at the address of the fingerprint. The interpretive information could also optionally be non-numeric information, which could include for example a map of anomalous results from the experimental or "wet" fingerprint assay to the probabilistically correct interpretation of such anomalous results.

Figure 3:
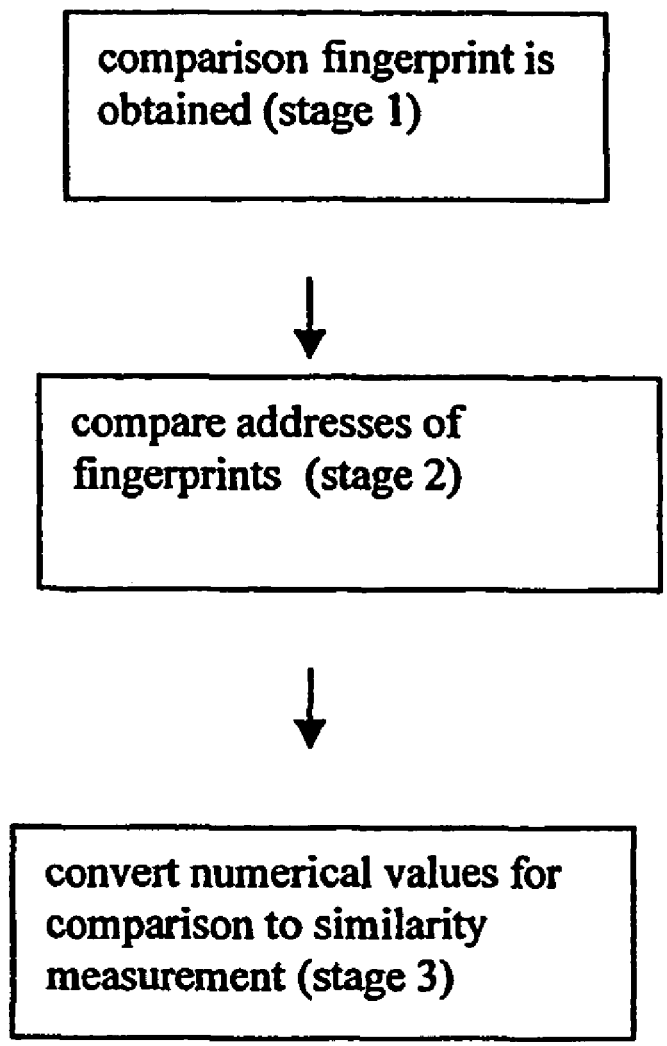
FIG. 3 is a flowchart of an exemplary method according to the present invention for comparing the fingerprint of the sample carbohydrate polymer to at least one other fingerprint.

Next, optionally and preferably, a comparison method is performed for comparing the fingerprint of the sample carbohydrate polymer to at least one other fingerprint. More preferably, the fingerprint for comparison is obtained from a standard, known carbohydrate polymer, although alternatively, the other fingerprint could also optionally be obtained from another sample carbohydrate polymer. An example of such a method is described with regard to FIG. 3.

In stage 1, the comparison fingerprint is obtained. As previously described, the comparison fingerprint is preferably obtained from a standard known carbohydrate polymer. Regardless of the source of the fingerprint data, however, preferably the comparison fingerprint data includes information about the experimental conditions, including at least the set of saccharide-binding agents which were used to obtain the data, and more preferably including such information as washing conditions, stringency of the incubation conditions, the type of label on the solubilized saccharide-binding agent, and so forth.

In stage 2, the actual address(es) of the fingerprints are compared. Optionally, the comparison is performed address by address, with at least a positive result of the comparison being given a positive numerical value. More preferably, a negative result of the comparison is given a negative numerical value. Stage 2 is then preferably repeated for all addresses which are to be compared.

In stage 3, the total numerical values for the address-by-address comparison are preferably converted to a similarity factor according to some function. The function is optionally simple, for example by adding all of the positive and negative values from the address-by-address comparison process. Alternatively and preferably, the results can be weighted. More preferably, the results are weighted according to the previously described interpretive information from the experimental conditions, such that a greater weight could optionally be given to the result of a comparison between two addresses of the fingerprints in which more certainty can be assigned to the experimental result, for example.

An example of a quantitative tool for comparing two fingerprints optionally and more preferably employs phylogenetic analysis, which has the advantage of returning a distance between two or more fingerprints, as opposed to a simple numeric measurement of $$S = \sum_{i=1}^{N} \sum_{j=1}^{Ci} Vi \tag{1}$$

similarity/dissimilarity. Originally used for examining evolutionary relationships between biological sequences, such as protein or DNA sequences for example, phylogenetic analysis provides a quantitative measure of the distance, or the degree of difference between two or more sequences. The use of phylogenetic analysis is particularly preferred for the optional but preferred embodiment of the present invention, in which the fingerprint of the sample carbohydrate polymer is compared to a database containing a plurality of such fingerprints. More preferably, the fingerprint data is for standard carbohydrate polymers. In any case, for this preferred embodiment of the present invention, stage 3 is replaced by a different function, which optionally requires stage 2 to be repeated for each fingerprint in the database.

Since phylogenetic analysis has been investigated for many years, and is a well-known topic in the art, many different methods are known in the art. In addition, a variety of companies offer a variety of products and utilities for analyzing phylogenetic information.

According to the present invention, optionally and more preferably, the following function is used for calculating phylogenetic information, in which the information of the fingerprints is expressed as a matrix of distances. These distances are optionally obtained according to some known function, such as a Hamming function, for example. According to a preferred embodiment of the invention, the distances are obtained as follows:

$$D = \sum_{i=1}^{N} \sum_{j=1}^{C} Vi \tag{4}$$

Where:
D is the expression for the distance;
N is the number of addresses in fingerprint1 and fingerprint2;
C is the maximum number of colors that can be distinguished in address i of the fingerprints;
Vi is 1 if a color that found in address i of fingerprint1 exists in the same address i in fingerprint2, otherwise Vi is zero.

Once fingerprint data has been stored in the database in a numerical format, for example as strings of numbers, an advanced comparison analysis may be performed to find related groups or families of fingerprints. A preferred method for such analysis is hierarchical clustering (see for example A. K Jain and R. C. Dubes, 1988; *Algorithms for Clustering Data*. Prentice-Hall, Englewood Cliffs, which is hereby incorporated by reference as if fully set forth herein). The fingerprints may also optionally be transposed, so that the transposed fingerprints would contain all values recorded on the same relative address for different sample polymers. In other words, the transposed fingerprint data would represent a vector of the lectin data. Clustering analysis of the transposed fingerprints may optionally be used to reveal relations between the binding properties of saccharide-binding agents.

The previous Figures described some basic tools for obtaining experimental fingerprint data, and for comparing fingerprint data between two or more carbohydrate polymers. The next Figures describe methods for deriving higher-level information from the fingerprint data, such as maps which characterize the sample carbohydrate polymer, for example. The method of each subsequent Figure enables increasing higher levels of information to obtained, and also optionally allows maps or other characterizations of the sample carbohydrate polymer which do not fit the experimental data to be eliminated. Preferably, at each higher level, additional experimental data and analyses are incorporated into the process for obtaining and examining the maps, in order to characterize the sample carbohydrate polymer as much as possible, and also in order extend the useful information which can be derived from individual experiments.

Figure 4:
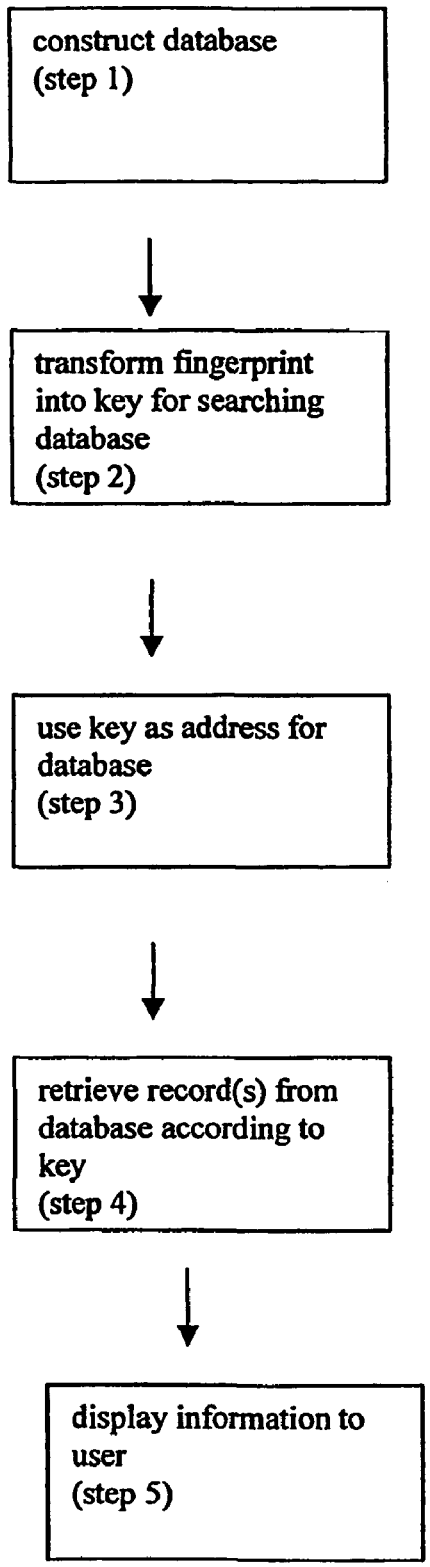
FIG. 4 is a flowchart of an exemplary method according to the present invention for using the fingerprint of the sample carbohydrate polymer as a key for searching through a database of fingerprint data for standard, known carbohydrate polymers.

Optionally and more preferably, the fingerprint of the sample carbohydrate polymer is used as a key for searching through a database of fingerprint data for standard, known carbohydrate polymers, as described with regard to the method of FIG. 4. As previously described, the fingerprint of the sample carbohydrate can optionally be compared to other fingerprints, for example according to a similarity function and/or a distance (phylogenetic) function. The exemplary method of FIG. 4 extends this option with a preferred implementation for performing many such comparisons more rapidly and efficiently.

As shown, in stage 1, the database is constructed in order to permit the fingerprint to be used for addressing the database. For example, preferably the database is constructed such that each address of a record in the database is found as the coordinates of a multi-dimensional array. Each record, in turn, corresponds to a fingerprint. Each address of the fingerprint, corresponding to a particular type of data, would then be a coordinate of the multi-dimensional array. By matching at least a portion of the coordinates to at least a portion of the fingerprint of interest, a match could optionally be more easily found.

Alternatively, the database is constructed as a relational database, in which portions of the fingerprint are still used for addressing the database but in separate segments. For example, a first part of the relational database could optionally hold information for a particular class of saccharide-binding agents. Within this first part, information could optionally be stored for specific saccharide-binding agents. Pieces of the fingerprint of the sample carbohydrate polymer would then optionally be used to sequentially penetrate to the specific information of the database.

In stage 2, the fingerprint data for the sample carbohydrate polymer is transformed into a key for searching through a database. Optionally and preferably, the key is in the form of a linear string. If the fingerprint is already in the form of a linear string, then optionally this stage is not performed. If the fingerprint is in the form of a plurality of records, then preferably such data is combined to form the linear string. For example, the data may be in such a format of a plurality of records according to one optional embodiment which, as previously described, combines interpretive experimental data with the actual fingerprint in separate records. Such data may optionally be transformed into the linear string by first modifying the fingerprint itself, as described for example with regard to FIG. 2 above. Alternatively, the experimental interpretative data may optionally be given a numeric value for each type of such data, and then added as an address to the linear string of the fingerprint.

In stage 3, the linear string, or other key, for the fingerprint is preferably used as an address for the database. Depending upon the structure of the database, the linear string may directly form the address of the record(s) of interest, for example if the database addresses are determined according to the coordinates of a multi-dimensional array. Alternatively, segments of the linear string may optionally be used to determine which information is of interest, for example through a recursive search through the hierarchical structure of the records of the database. Also alternatively, the linear string may optionally be further processed by a hashing function, the result of which would form the address of the record(s) of interest, such that the database address structure would optionally feature a hash table.

In stage 4, the record(s) of interest are retrieved from the database according to the fingerprint of the sample carbohydrate polymer. Optionally and preferably, the information from the record(s) includes identifying information for the comparison carbohydrate polymers, the actual fingerprints of these carbohydrate polymers, and experimental conditions and other interpretive information.

In stage 5, the information from these record(s) of interest is preferably displayed to the user, for example through some type of GUI (graphical user interface).

Section 2: Analysis of the Fingerprint Data for Characterizing a Carbohydrate Polymer According to preferred embodiments of the present invention, the fingerprint of the sample carbohydrate polymer is itself internally analyzed in order to extend the fingerprint data, as described with regard to the method of FIG. 5. According to this exemplary method, the fingerprint addresses are first recursively analyzed in order to find simple maps, or map fragments. Next, these map fragments are assembled to larger maps, again preferably through a recursive analysis. Optionally and more preferably, the maps are transformed into property vectors, or property descriptors, for use in QSAR (quantitative structure-activity relationship) algorithms. This translates the fingerprint data into a set of numbers directly describing structural properties (i.e., the level of sialic acid content, the existence or absence of certain monomers or dimers, and so forth). QSAR can in turn optionally be used for activity prediction in molecular drug design.

Figure 5:
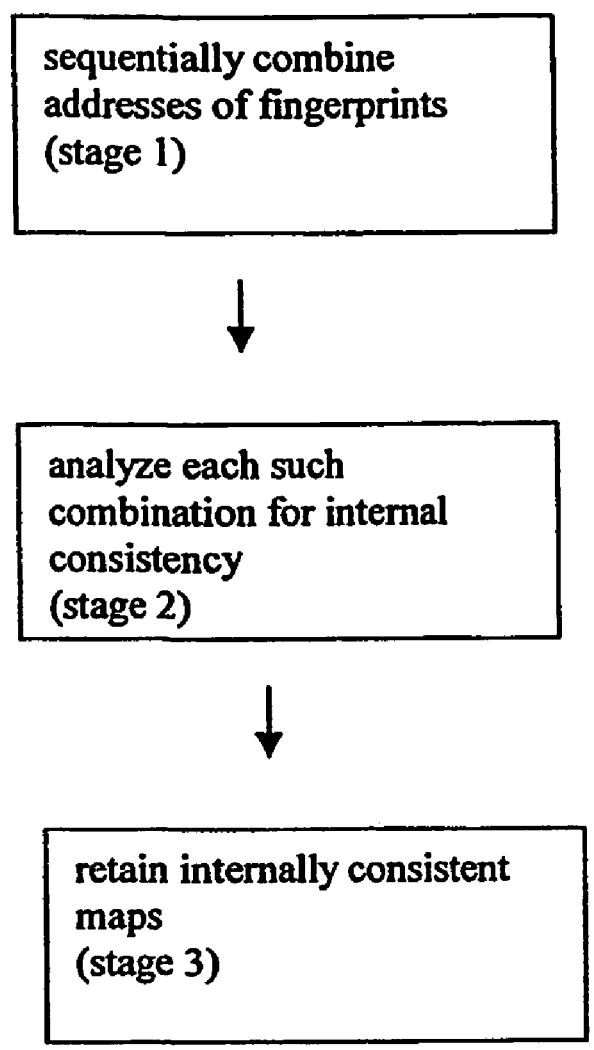
FIG. 5 is a flowchart of an exemplary method according to the present invention for internally analyzing the fingerprint of the sample carbohydrate polymer in order to extend the fingerprint data.

As shown with regard to FIG. 5, in the first stage of the method, a first set of maps which characterize the sample carbohydrate is preferably created, optionally through recursive analysis of the fingerprint data. Such a recursive analysis may optionally simply take the form of sequentially combining each address of the fingerprint with a sequence of one or more other addresses in stage 1. Next, in stage 2, each such combination is analyzed in order to determine if the map (or map fragment) is internally coherent. In stage 3, those maps or map fragments which have been shown to be internally coherent are retained for the next level of analysis.

As an example for this type of analysis, a map may obtained from an experiment in which the sample carbohydrate polymer is first digested with a cleaving agent, and in subsequent stages reacted with binding agents. Such an assay is described in more detail with regard to PCT Application No. PCT/IL00/00256, previously incorporated by reference in its entirety. However, as a brief example, a sample carbohydrate polymer which is labeled at the reducing end is reacted with a first saccharide-binding agent, which may optionally be a glycosidase with the recognition sequence a. In a control reaction, the labeled sample carbohydrate polymer is left untreated. The reactions are then independently further reacted with an immobilized saccharide-binding agent, which may optionally be a lectin with the recognition sequence b. After washing off unbound sample carbohydrate polymer, a detection stage is carried out. The presence of the label indicates that site b is present in the sample carbohydrate polymer.

By comparing reactions where the first saccharide-binding agent is present, with independent control reactions where the first saccharide-binding agent is absent, the effect of the glycosidase on the presence of the label can be determined. For instance, if the label is detected in the control reaction after binding to the lectin with recognition sequence b, but not in a reaction where the first saccharide-binding agent is a glycosidase with the recognition sequence a, the sequence of recognition sites is b-a-reducing end. On the other hand, if the label is present in both control and glycosidase reactions, this indicates that the sequence of recognition sites is a-b-reducing end. The recognition site a may not be located inside the sample carbohydrate polymer, i.e., may not exist in the saccharide sequence.

According to preferred embodiments of the present invention, stage 1 of the method shown in FIG. 5 is performed by first placing each address of the fingerprint as a node on a hierarchical tree. Depending upon the type of data which is represented by the fingerprint address, the address may optionally appear on more than one node. Preferably, the hierarchy of the tree is constructed according to a plurality of categories of data. For example, part of the tree may optionally represent simple binding of the saccharide-binding agent to the sample carbohydrate polymer. This part of the tree would then be preferably structured according to characterization of each saccharide-binding agent, for example according to the type of agent (lectins, antibodies, etc.), the effect of the agent on the sample carbohydrate polymer (binding, cleavage, etc.), the type of label for the solubilized saccharide-binding agent.

Next, in stage 2, the tree can be recursively examined by using each address of the tree as the root node, for example, or alternatively by traveling from each node of the tree to the other nodes of the tree to establish the map or map fragments. The advantage of this method is that if the tree is constructed according to biologically useful categories and/or parameters, the maps which are constructed from the nodes of the tree should be internally coherent. This process may optionally be repeated a number of times in order to construct larger maps.

Preferably, multiple types of fingerprint data are incorporated into these maps, optionally also including fingerprint data which involves the modification of the sample carbohydrate polymer before the assay is performed. For example, the polymer could optionally be modified with glycosidases for cleaving the molecule; elimination of reducing ends; and with glycosyltransferases for adding one or more saccharides, optionally with a label, to the sample carbohydrate polymer. Modification with saccharide(s) having a label is particularly preferred for "double-label" experiments, in which the second saccharide-binding agent of the assay of FIG. 1 would have the second label. The map of the two labels would thus provide additional information concerning the structure of the sample carbohydrate polymer.

It should be noted that these different types of experimental data may optionally be incorporated into a single fingerprint for the sample carbohydrate polymer, although such incorporation is not necessary. Alternatively, the different types of data may be used as an adjunct to the fingerprint for creating the maps for the polymer. In any case, these different types of experimental data should be obtained from experimental assays performed on at least similar experimental material, with at least similar conditions. More preferably, the experimental material and conditions are identical, particularly for comparisons between different polymers, such as between a standard, known carbohydrate polymer and the sample carbohydrate polymer.

Optionally and more preferably, the maps are transformed into property vectors, or property descriptors, for use in QSAR (quantitative structure-activity relationship) algorithms, for example. Each property vector is a quantitative description of structural properties and/or features of the sample carbohydrate polymer. Each numeric value in the vector preferably corresponds to a particular property or feature, such as the level of sialic acid content, the existence or absence of certain monomers or dimers in the carbohydrate sequence, and so forth). Such a property vector could also optionally feature data for describing more qualitative properties.

The process of translation is preferably performed by correlating a plurality of numeric values of the fingerprint in order to build the map. Such a correlation is optionally performed by comparing the fingerprint data to a "template", in order to determine if the property or feature exists. Alternatively, the value in the property vector could optionally be obtained by integrating results from other types of experiments, as described in greater detail with regard to FIG. 4 below. For example, the value in the property vector could optionally be derived from the saccharide content of the sample carbohydrate polymer.

Such additional information may enhance the data interpretation in a number of respects. First, it can optionally be used to eliminate impossible or at least highly improbable recognition sites from those sites which have determined to be possible sites from the different types of experimental assays. For example, for assays in which lectins are used as a saccharide-binding agent, many lectins specifically bind to both glucose (Glc) and mannose (Man), yet many glycans do not contain Glc. Thus, the presence of binding to these lectins indicates the presence of Man alone.

In addition, such information can optionally suggest ambiguities in data interpretation, and add information that is not present in the data. An example of the latter function would be the detection of the presence of Kdo, which is a monosaccharide in LPS (lipopolysaccharides), yet may not be detected according to lectin binding data. Such information may also present a strong clue to confirm/reject certain hypotheses.

Such information should not be limited to monosaccharide composition, however, as this is only intended as a non-limiting illustrative example. Instead, this information may optionally include data from experimental assays; structural information, such as how many length species are created by a certain cleavage of a polymer, medical and origin information, since for example mammalian carbohydrate polymers are more limited in monosaccharide composition then plant carbohydrate polymers, and both are more limited than bacterial carbohydrate polymers.

Figure 6:
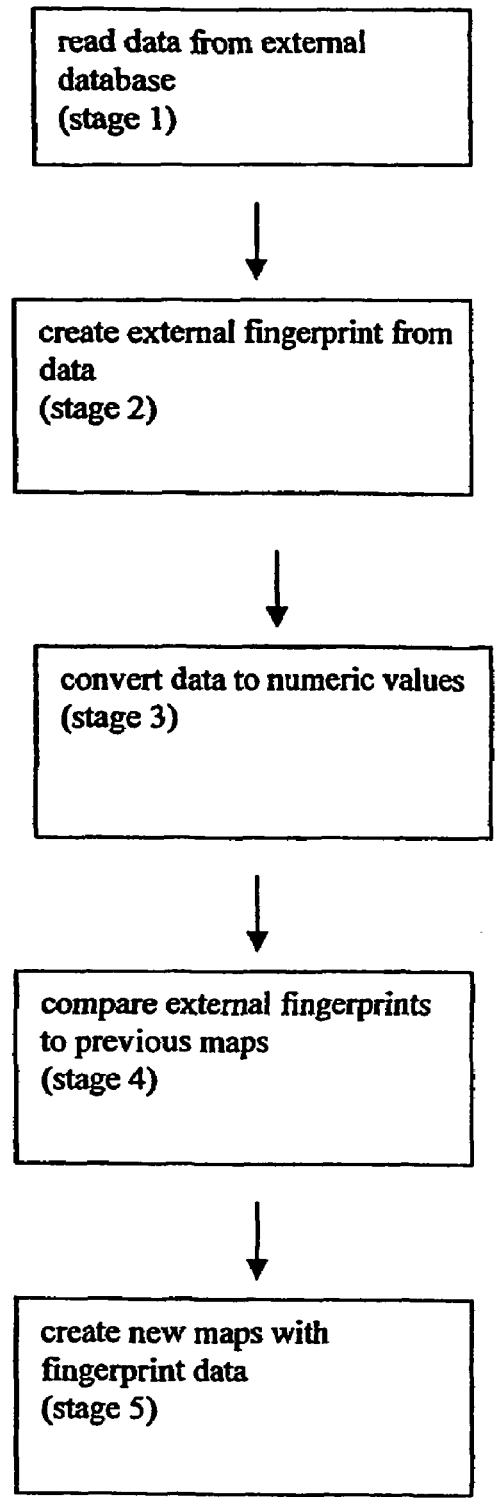
FIG. 6 is a flowchart of an exemplary method according to the present invention for extending the fingerprint data by integration of data from external databases.

FIG. 6 is a flowchart of an exemplary method according to the present invention for extending the fingerprint data by integration of data from external databases. By "external databases", it is meant that the data is obtained from experiments which are not performed on the same material, such that the same experimental conditions do not necessarily apply to both sets of data. Such information could be related to the composition of the saccharide, its source, and possibly other information as well.

For example this information could include whether the sample carbohydrate is part of a glycoprotein, the use of other types of carbohydrate binding agents such as cytokines, and so forth. The introduction of such data is preferably performed at least partially with information from known carbohydrate polymers, such as EPO, for example, as a standard, reference carbohydrate polymer.

As shown with regard to FIG. 6, in stage 1, the data is read from the external database, and the format of the data is analyzed. In stage 2, if the format of the data includes one or more numerical values which characterize specific aspects of the polymer, then these values are optionally used to create a "fingerprint" for the sample carbohydrate polymer. For example, if an assay has been performed with the sample carbohydrate polymer to determine the saccharide content, then the relative amounts and identity of the different types of saccharides are clearly convertible to a fingerprint of such data. This conversion is possible at least partially because the relative number and type of variants of saccharides in a sample are known, or at least may be estimated.

For example, there are rules limiting the possible structures of glycoprotein oligosaccharides to two distinct families known as N-glycans and O-glycans. Each family has a set of combination rules, limiting the possible structures to a computationally manageable number. Some of these rules, or typical structure types, can be found in standard textbooks of glycobiology (e.g., Varki et al., 1999, Ch. 7,8). For example, the reducing end of N-glycans is almost always composed of the same identical pentasaccharide known as the 'core.' A fucose residue may be connected to this core, bound at a single allowed location and conformation. Farther away from the reducing end, the core may connect to what is known as 'antennae' composed of alternating Galactose-N-acetyl-Glucosamine pairs, or to several mannose residues.

In addition, for specific materials even stricter limitations are known from previous studies. For example, for the glycoprotein known as Ricinus Communis agglutinin (RCA-I), all researchers to date have found that the N-glycans are of the oligomannose type (possibly having a xylose residue as well) and have no antennae (Kimura et. al, 1987, 1990).

One or more, but preferably all, of these limitations are optionally and preferably converted to mathematical rules. The rules can be used to express and manipulate oligosaccharides of a known family mathematically. For example, N-glycans can be expressed as vectors, whose elements are numbers or functions representing the amount of glycan subunits allowed by the rules (see Table 1). They can also be expressed as hierarchical trees of numerical values, where tree structure is determined by the hierarchy of the rules (see Table 2).

Incorporation of the limitation rules therefore supports the efficient performance of mathematical operations on sets of numbers representing glycan properties. Such operations include and are not limited to: comparison, multiplication, averaging, clustering. Furthermore, these rules greatly limit the space of allowed variants, compared to the theoretical combinatorial space.

Alternatively, in stage 3, if the format of the data includes raw experimental results, such as a map of bands on a PAGE (polyacrylamide gel electrophoresis) gel after cleavage of the carbohydrate polymer with a glycosidase for example, then the data is preferably converted to one or more numeric values. For example, the map of bands could optionally be converted by determining the presence or absence of a band at a particular molecular weight, and then creating a "fingerprint" with binary values (positive/negative) at each molecular weight Alternatively, the fingerprint could optionally include the series of molecular weights for the bands as a sequence of numerical values. It should be noted that PAGE gel assays are intended only as a non-limiting example, and that other types of assay data could also optionally be incorporated, such as column chromatographic data for example.

The format of the data may also optionally include two different types of experimental results, which would then preferably be correlated in order to form the fingerprint. For example, the PAGE gel assay could be performed with the addition of end labeling with various types of glycosyltransferases or other end-labeling mechanisms. The gel would then contain two types of data: the presence of bands at specific molecular weights; and the presence of specific labeled bands. The fingerprint could then optionally be created to indicate both types of data as numeric values, for example as the molecular weight of the bands with binary (positive/negative) values for indicating the effect of labeling.

In stage 4, these fingerprints are preferably compared to the maps which were derived for the sample carbohydrate polymer from the previous level in FIG. 5. If any of these maps are inconsistent with the additional fingerprint data, they are optionally and preferably eliminated. For example, lectin-binding information may indicate the possibility that the monosaccharide Fuc (fucose) is absent. On the other hand, such a possibility may be directly contradicted by the monosaccharide composition of the carbohydrate polymer, which may indicate the presence of Fuc. In such a situation, the addition of the latter data may optionally indicate that a map which does not include Fuc should preferably be eliminated as being inconsistent with the additional data.

In stage 5, optionally and more preferably, the additional fingerprint data is used to create new maps. These new maps are most preferably created according to the method of FIG. 5, which is suitable for use with fingerprint data of this format, regardless of the source of the experimental data.

Both the optional creation of new maps and the optional elimination of existing maps are examples of the examination of the probability space for the carbohydrate polymer. Unlike for the method described below, these maps may still optionally be directly related to the fingerprint or other experimental data. However, the probability space is more difficult to search than for other types of biological polymers, such as DNA for example, since there is no requirement for accuracy of the experimental data, but only for reproducibility. Thus, the probability or combinatorial space is increased even beyond that which is searched for other types of biological polymers.

Figure 7:
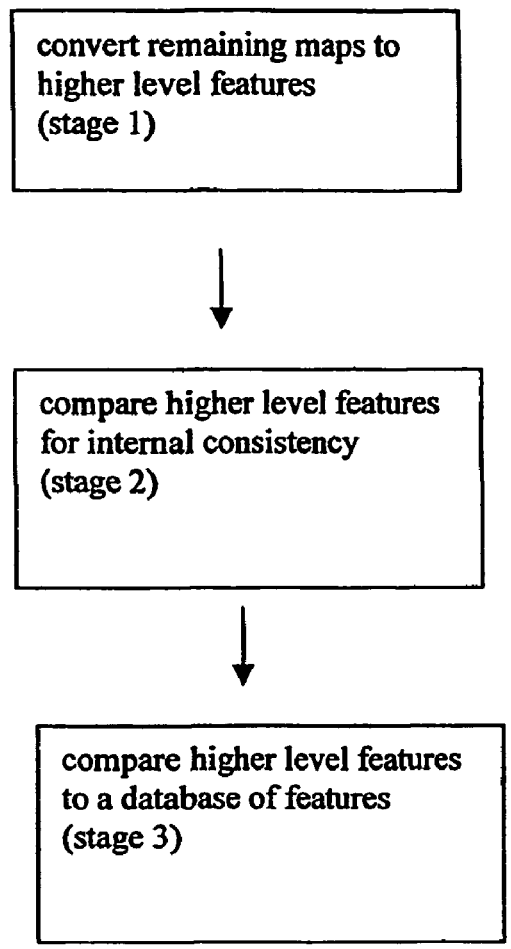
FIG. 7 is a flowchart of an exemplary method according to the present invention for locating features of interest within the sample carbohydrate polymer.

FIG. 7 is a flowchart of an exemplary method according to the present invention for locating features of interest within the sample carbohydrate polymer. By this point, the maps should no longer include any reference to the original raw data, but instead should be composed of sequences of elements. Some raw data may not yield any useful information. The sequences of elements can now be compared to a three-dimensional database, which stores pieces of three-dimensional (structural) information.

This process is actually a combinatorial search, or a search in combinatorial space, since each of the maps represents a possible combination of related elements for describing the sequence, structure, function, or some combination thereof, of the carbohydrate polymer. These maps can in turn be used to search for different higher-level features of the carbohydrate polymer, which are related to particular sequences, structures and/or functions of interest within the polymer.

As shown with regard to FIG. 7, in stage 1, the remaining maps are first converted to higher-level features, if necessary (this stage may optionally have already been performed as part of the process of creating the maps). For example, the maps are preferably converted to conform to various functional epitopes and/or sequence-based features, as well as to characterization features. This stage is particularly aided by the presence of data from previous comparisons to standard reference carbohydrate polymers, since such comparisons are particularly useful for locating functional features.

These features of interest may optionally be short sequences or portions of sequences of monosaccharides within the larger polymer sequence. A very simple example of such a feature is a glycosidase recognition site. Such features may also optionally be described as "sequence-based" features, in that they are characterized by at least a portion of the sequence of the carbohydrate polymer. Such features have the disadvantage of requiring absolute accuracy of the experimental data, rather than mere reproducibility. However, they have the advantage of being comparable over a wide variety of different known carbohydrate polymers, through data obtained from external databases as previously described.

Alternatively and/or additionally and preferably, these features of interest concern functional epitopes and/or sequence-based epitopes having a biological function of interest. By "functional" epitope, it is meant that at least a portion of the carbohydrate polymer appears to be associated with a particular function and/or type of function, regardless of the actual sequence of the carbohydrate polymer. Such a functional epitope may optionally be located through the performance of the same assay on a plurality of carbohydrate polymers, with only the requirement of reproducibility, rather than absolute accuracy. Of course, the functional epitope may also optionally be characterized by a sequence, such that the same epitope may optionally be both a sequence-based epitope and a functional epitope.

Also alternatively and/or additionally and preferably, these features of interest concern "characterization" features. These features are not necessarily discrete portions of the carbohydrate polymer, but rather are indicative of the classification, function or nature of the overall polymer, or some combination thereof For example, such a characterization feature may enable the carbohydrate polymer to be determined to be "EPO-like". This determination would not necessarily immediately result in the location of specific functional epitopes within the polymer, for example, but may provide an indication that the carbohydrate polymer should be further examined for the possibility of such functional epitopes being present.

In stage 2, these higher-level features are compared for internal consistency. If any two such features are inconsistent or mutually exclusive, then optionally and preferably, both such features are removed from further consideration, as it is not possible to determine which is correct. However, if further data becomes available, then alternatively one of the features could be retained, according to the data, for example as previously described.

In stage 3, the higher level features are compared to a database of such features, which is preferably embodied as a three-dimensional database containing structural and/or functional components of carbohydrate polymers. For example, such a feature could optionally be used to locate an epitope of interest, which could then provide information concerning the type or function of the sample carbohydrate polymer.

Section 3: Specific Analysis of Mixtures of Carbohydrate Polymers

The previous sections described methods for obtaining raw experimental data for fingerprint assays, and then managing and analyzing this data. This section concerns a method for analyzing data related to a mixture of a plurality of carbohydrates and/or carbohydrate-containing materials, which may optionally be used in conjunction with the previously described experimental and analytical aspects of the present invention. The data is analyzed to determine the presence of one or more different such materials, optionally and more preferably glycoproteins. The method preferably obtains a population or frequency distribution between the possible combinations and/or variants within the mixture of materials. More preferably, the method is based upon a priori knowledge which provides at least partial identification information, such that at least a portion of a carbohydrate structure is identified according to this knowledge. The method then more preferably combines a plurality of different experimental results in order to provide information about the mixture of carbohydrate-containing material.

The method is particularly useful for materials such as glycoproteins, which are typically found as a plurality of variants, often as a heterogeneous mixture of several combinations of these variants. The composition of such a mixture of variants may optionally and preferably be determined according to data obtained from fingerprint data, as previously described, and/or other analytical methods, according to the method of the present invention.

According to a preferred embodiment of the present invention, the method is started by identifying and limiting the variant space of the material. By variant space, it is meant the possible combinations of one or more carbohydrate polymers and/or other carbohydrate materials which may be present in the mixture, with their variants. Each variant may exhibit slight changes from the main type of carbohydrate material. Limitation of the variant space may optionally and preferably achieved by identifying all structural limitations on the glycans in the mixture, and formulating them as mathematical rules, as explained in the previous section. The collection of allowed variants in the mixture are then optionally and preferably represented as property vectors whose elements correspond to allowed configurations.

Once the number of possible glycans has been preferably limited to a manageable magnitude, the quantities of each variant in the mixture are then preferably identified. For such identification, an algebraic problem with a finite number of unknowns is obtained, where each unknown corresponds to the abundance value of a possible glycan variant. If the experimental method to be used is a sandwich-pair method such as the preferred embodiment of the fingerprint assay, an unknown for each pair of reference glycans (on the same glycoprotein molecule) can optionally be located from the possible variant space.

In any case, the collection of possible unknowns for the material in question is termed herein the "candidate set". The method of the present invention therefore preferably obtains the relative abundance of each member of the candidate set.

If the size of the candidate set is C, then the relative abundance may be determined as an algebraic problem with C unknowns. C−1 independent equations are required to solve for the unknowns. These equations take the generic form:

$$f_i(\vec{X}) = R_i, i = 1 \ldots E, E \geq C - 1 \quad (1)$$

$$\sum_{k=1}^{C} X_k = 1,$$

where X is a vector of length C, whose elements represent the abundance values of reference glycans (or glycan pairs) in the candidate set The right-hand side of the equations in (1), that is the $R_i$'s, represents results of laboratory experiments. The left-hand side, the $f_i$'s, represents the model or prediction of the experimental results on member of the candidate set. This is possible because the members of the candidate set correspond to reference glycans (or glycan pairs) of a known structure. Of course, constructing the model requires knowledge of the experiment's mechanism. Such knowledge is usually available for standard methods. In the absence of such knowledge, a satisfactory model can optionally and preferably still be constructed. The ability to construct such a model in the absence of such knowledge is considered to be one aspect of the present invention, as described in greater detail below.

If the mechanism of the experiment is such that the experimental result is linearly proportional to the abundance of each glycan variant in the mixture, the equations in (1) become linear. This assumption is made for all of the equations described below. Equation (1) then becomes $$\vec{A}\vec{X} = \vec{R} \quad (2)$$

$$\sum_{k=1}^{C} X_k = 1,$$

where X is as before, R is a vector of length E, and A is a matrix of dimensions E×C. A is also known as the "model matrix."

For experiments such as HPLC or MS, the data represented by each experimental peak can optionally be converted to a linear equation. The right-hand side of the equation represents the peak's integrated intensity, while the left-hand side is a simple binary vector with 1's in elements corresponding to glycan variants that are expected to contribute to the peak (according to their properties) and 0's in all other elements.

For array-type experiments such as fingerprint assays, the data represented by each spot may be converted to an equation. The right-hand side represents the normalized spot intensity. The left-hand side is a vector composed of coefficients, each representing the expected reaction intensity for the reference glycan, according to standard chemical equilibrium formulas and literature data. Table 3 shows a compilation of literature data about lectin affinities into the format that represents glycans as vectors. This compilation yields vectors of normalized lectin affinity, which can conveniently be multiplied by the reference glycan vector. These vectors indicate agent specificity to different subunits and/or substates of the glycans within the total search space. The result is the predicted intensity of lectin-glycan reaction.

Representing the mixture composition problem as a matrix-vector equation provides a variety of standard mathematical methods to solve the equation and to optimize laboratory work. Since the equations are based on comparing models of experiments to the experiment results, there is an inevitable error associated with each equation. Therefore, according to a preferred embodiment of the invention, the equations are not solved as an exact set, but instead are used to minimize the overall error. This minimization can be done using the standard method of conditional (or constrained) least squares (Powell, 1983). In this method, equation (2) is converted to the form $$\vec{X}^T \vec{C} \vec{X} + 2\vec{D}\vec{X} \to \min \quad (3)$$

$$\sum_{k=1}^{C} X_k = 1$$

$$0 \leq X_i \leq 1, i = 1 \ldots C,$$

where C is the covariance matrix of A, and the elements of D are minus the inner product between R and the corresponding column of A (the i, j element of a covariance matrix is the inner product between column i and column j of the original matrix). This method finds the solution for X that minimizes the sum of squares of the errors, under the given constraints. Algorithms to implement this method are common in the art, and may be easily selected and implemented by one of ordinary skill in the art. It is also known as 'convex quadratic programming.' If the experimental errors are known, weights can be introduced to ensure that the algorithm considers the relative error of each experiment. This method is known as 'weighted least squares.'

Figure 8:
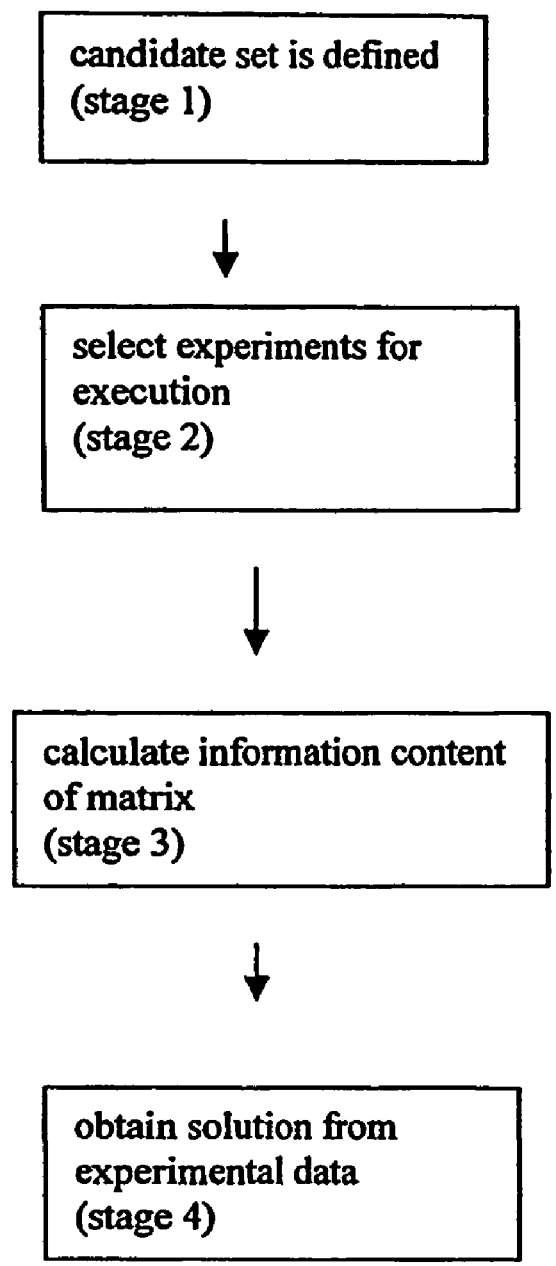
FIG. 8 is a flowchart of an exemplary method according to the present invention for analyzing a mixture of carbohydrate-containing materials.

FIG. 8 shows a flowchart of an exemplary method for analyzing the experimental data according to the present invention. In stage 1, the candidate set (collection of reference glycans or glycan pairs) is preferably defined. Knowledge of generic limitations on variant space is incorporated into the information, whether in the form of rules or otherwise, optionally and preferably in addition to specific limitations which are known for this material (shown in stage 1). From the chosen experimental method, knowledge about the detection resolution limits and also about the form of the unknowns is derived (stage 2). For example, if mass spectrometry is used, the unknowns may be defined as representing groups of single glycans that are indistinguishable by MS. If fingerprint assays are used, the unknowns should represent pairs of glycans, in a representation which corresponds to the detection agents (e.g., lectins) used.

Additionally, user preferences such as the maximum desired number of unknowns are optionally and preferably considered. Also optionally and preferably, knowledge from previous iterations of the method according to the present invention is incorporated. This knowledge assists in the elimination of groups of variants from the candidate set.

Using all this information, preferably an optimal set of unknowns is chosen in stage 3. This may optionally be done manually using human judgment, but preferably is performed by a software program which is coded with an appropriate optimization algorithm such as linear goal programming (e.g., Winston, 1991, Ch. 14).

Turning back to FIG. 8, in stage 2, optionally and preferably, one or more experiments are chosen for execution. The first screening examines how adequate is the experiment for the glycan variant mixture in question. This is done by quantifying the model coefficients of each potential experiment per each unknown, from stage 1.

An optional and preferable example for calculation of the model coefficients for the fingerprint assay is provided here. Tables such as Table 3 present the relative equilibrium affinity (in arbitrary but consistent units) of lectins and other agents to glycan subunits, according to a chosen vectorial representation of glycans. To find the relative amount of lectin-glycan complexes for a given glycan variant, we multiply each element of the variant by the corresponding affinity element:

$$[LG] = k \vec{L}^T \vec{G}, \quad (4)$$

where [LG] is the number of complexes in equilibrium, the vectors on the right-hand side are the parameterized vectorial representation of lectin affinity and glycan, as explained previously, and k is a factor converting from arbitrary to real units.

Since a preferred embodiment of the fingerprint assay is a sandwich assay using two lectins, as previously described, a second reaction between a second lectin and another glycan on the same molecule is necessary. Prediction of the fingerprint assay reaction intensity on a given molecule involves a multiplication of two products in the form of (4), and also normalization and conversion factors. The model coefficient assumes the form:

$$C_{ij} = \frac{m_T^{(b)}}{2} \left( T_i^{(b)} B_j^{(a)} + T_j^{(b)} B_i^{(a)} \right) \quad (5)$$

where here the indices i, j indicate a pair of glycans i and j that together constitute a glycan variant represented by a single unknown. $B_i^{(a)}$ is the predicted reaction intensity between glycan i and bottom lectin a, received by multiplying their vectors as in (4). Similarly, the other coefficients in the parenthesis on the right-hand side represent intensities of bottom lectin with glycan j, and of top lectin with each glycan. The factor $m_T$ indicates an optional and preferable factor to account for the number of glycans on the same molecule.

Once all coefficients for a given experiment are calculated, a model vector of length C (the number of unknowns) is obtained for the experiment. If the norm of this vector is less than a given threshold, it means that the experiment will probably not yield significant results, and it is discarded (stage 2). At this stage, a metric (such as standard deviation) is calculated to quantify the differences between the vector elements. If the value of the metric is too small, the experiment may yield results, but it cannot help to distinguish between unknowns, and it is also preferably discarded.

Experiments passing these two initial tests are preferably subject to the second, more advanced screening, by combining all experiment models to create a matrix (essentially identical to matrix A of equation (2)). A measure of the potential information content of the matrix is calculated in stage 3. This can optionally be the negative of the determinant of its covariance matrix, or of its Fischer information matrix. This measure is used to seek a combination of E experiments that maximizes the information delivery potential.

After the set of E experiments is chosen and performed, stage 3 of FIG. 8 is performed. Experimental data is preferably collected, and converted to the right-hand side of the equation set. This conversion may involve multiplication by factors affected by the molar mass, of the material in question, and other similar factors. In the absence of a clear conversion factor between the units of the model A and the results R, an implicit scheme may optionally be used to find the optimal conversion factor as the (C+1)th unknown. Accordingly, X is expanded by one element. The dimensions of A become E×(C+1), the last column being the negative of R. Equation 2 formally becomes:

$$[\vec{A} - \vec{R}]\vec{X} = 0 \quad (6)$$

$$\sum_{k=1}^{C} X_k = 1$$

Whatever the conversion scheme chosen, in the next step the matrices C, D (see equation (3)) are preferably calculated from the matrices A and R in stage 3. All other meaningful constraints such as those appearing in (3) are also converted to the solution algorithm's input format. The experimental errors may optionally be entered either as constraints or as coefficients in the calculation of C and D.

Once all data is in the correct format, a standard solution algorithm such as conditional least squares (convex quadratic programming) is optionally and preferably performed in stage 4. Alternative methods such as linear goal programming are also an option.

Once the results are received, an initial examination of the solution is optionally and more preferably performed. For example, the received values of X may optionally be entered as input to equation set (2), and the amount of error or correlation between the sides of the equations be measured.

If the correlation is below a given threshold value, some type of correction is preferably made. One example of such a correction is the removal of those experiments represented by equations that have the largest error. Another such correction may optionally be the addition or relaxation of certain constraints.

After the correction (if performed), all matrices are more preferably recalculated and the stage 4 is more preferably performed again. Once the correlation threshold has been reached, a stability check may optionally be performed by randomly removing a small number of equations, performing the calculation again and comparing the results to the original results.

Once the solution passes the initial integrity tests, stage 4 of FIG. 8 is performed. Result interpretation may optionally be performed first. The members of the candidate set may represent groups of glycans, subunits of glycans, characteristics of glycans, glycans, glycan pairs, or combinations thereof. Furthermore, the molecules in solution typically have several glycans each. In such cases, in order to more fully understand the solution, the results are optionally and preferably transformed the form of possible glycans or glycan combinations on the molecule, whichever is more convenient for the user.

One method for such a conversion is optionally and preferably performed by searching over a large database of glycans, or over the possible glycan combination space, and seeking the most likely glycan set that correspond to the characteristics found in the solution. This process may optionally be performed by using the mathematical method of quadratic programming as before, or by linear goal programming (see e.g. Winston, 1991, Ch. 14).

A use of linear goal programming for this transformation problem may optionally be described as follows. Assume that the glycan variants are in the form of glycan subunits (see Table 1), that is the unknowns represent abundance value of subunits. G is the set of all the glycans in the non-redundant database. U is the set of subunits. $A_{ug}$ is the percent of subunit u in glycan g. $X_u$ is a relative abundance of subunit u in the examined material, as found by our solution algorithm applied to experimental results. $Z_g$ is an unknown proportion of glycan g in the examined material. $e_u^-$, $e_u^+$ are the negative and positive deviations in u-th equation.

The basic transformation problem from subunits to glycans may then be defined according to the following equations:

$$\sum_{u \in U} (e_u^+ + e_u^-) \to \min \quad (6)$$

$$\sum_{g \in G} a_{ug} Z_g + e_u^+ - e_u^- = X_u, u \in U,$$

$$\sum_{g \in G} Z_g + e_{sum}^+ - e_{sum}^- = 1,$$

$$0 \leq Z_g \leq 1,$$

$$e_u^+, e_u^- \geq 0 \text{ for each } u$$

The first equation defines the goal of error minimization. The second represents the transformation from X to Z in the form of a rule on the glycans. The last three equations are standard constraints. Additional rules are preferably added to refine our choice of glycans. For a list of rules on a simulated problem, see Table 4. These rules are converted to equations and added to the basic equations in (6). For example, Rule 2 in Table 4 allocates percentages to subsets of the database, namely biantennary glycans, triantennary glycans, etc. Let B be the set of all biantennary glycans. The biantennary allocation of Rule 2 may be represented by the equation $$\sum_{g \in B} Z_g + y_B^+ - y_B^- = A_B, \quad (7)$$

where $A_B$ is the allocated percentage of biantennary glycans.

According to the optional but preferred method of the present invention, first results from all previous performances of the method of the present invention (if any), plus any additional knowledge about the material, are preferably formulated into rules or constraints on the glycans. Glycans are optionally and preferably represented as numerical entities such as vectors or trees containing subunits or properties (see Tables 1, 2). The members of the candidate set (whether they are subunits or other properties of glycans) are also converted to the same format Next, the linear programming algorithm searches for the set of glycans or glycan combinations which are most likely to be correct, given the abundance values found for the candidate set. Next, this set of glycans is selected from the data.

Now that the results are intuitively meaningful in the form of glycans or glycan combinations, they may be evaluated to determine whether they provide sufficient information about the examined mixture. If so, then a final report is optionally and preferably generated. If not, the method preferably returns to stage 1 of FIG. 8; optionally and more preferably the set of unknowns are refined or revised, and new experiments are optionally and preferably designed.

It will be appreciated that the above descriptions are intended only to serve as examples, and that many other embodiments are possible within the spirit and the scope of the present invention.

TABLE 1

N-Glycan subunits
This table shows a conceptual division of glycoprotein N-glycans into subunits. The division is based on knowledge of allowed and disallowed structures in N-glycans. Using this division, N-glycans can be represented as 21-element vectors.

| No. | Glycan-subunit name | Structure |
|---|---|---|
| 1 | GlcNac-GlcNac-beginning | GlcNac4-1($\beta$)GlcNac |
| 2 | Part of Pentasaccharide core | ($\beta$)Man[(6-1($\alpha$)Man(3-1($\alpha$)Man)] |
| 3 | Multi-Mannose | ($\alpha$)Man[(6-1($\alpha$)Man)(3-1($\alpha$)Man)] |
| 4 | Antenna Split 2,6 | ($\alpha$)Man[(6-1($\beta$)GlcNAc)(2-1($\beta$)GlcNAc)] |
| 5 | Antenna Split 2,4 | ($\alpha$)Man[(4-1($\beta$)GlcNAc)(2-1($\beta$)GlcNAc)] |
| 6 | No split | Gal3-1($\beta$)GlcNAc |
| 7 | Bisecting GlcNAc | ($\beta$)Man4-1($\beta$)GlcNAc |
| 8 | GlcNAc-Gal length elements | GlcNac4-1($\beta$)Gal |
| 9 | GalNAc replacing Gal | GlcNac4-1($\beta$)GalNac |
| 10 | Man 1-2 Man | Man2-1($\alpha$)Man |
| 11 | Without split | Man2-1($\beta$)GlcNac |
| 12 | 'Root' Fucose | GlcNac6-1($\alpha$)Fuc |
| 13 | Terminal or side Fuc1-3 | GlcNac3-1($\alpha$)Fuc |
| 15 | Sialic bound 2-3 | Gal3-2($\alpha$)NeuNAc |
| 15 | Sialic bound 2-6 | Gal6-2($\alpha$)NeuNAc |
| 16 | Terminal NeuGc | T-NeuGc |
| 17 | Terminal Gal | T-Gal |
| 18 | Terminal GalNac | T-GalNAc |
| 19 | Terminal GlcNac | T-GlcNac |
| 20 | Terminal Mannose | T-Man |
| 21 | Special | Gal 3-1($\alpha$)Gal |

TABLE 2

N-Glycan Rules
This table shows a formulation of the structural limitations on glycoprotein N-glycans in the form of hierarchical grammatical rules. Glycans can then be represented as hierarchical trees of numbers, each number corresponding to a state out of the allowed states for the given rule.

| Rule No. | Dependent on Rule No. | Code | # of Locations | States per Location | Deterministic Description |
|---|---|---|---|---|---|
| 1 | none | core | 1 | 1 | Glycan starts from Reducing end with a fixed 5-sugar. 2 GlcNAc's and then a mannose triangle. Most glycan diversity continues from the two external mannoses |

TABLE 2-continued

N-Glycan Rules
This table shows a formulation of the structural limitations on glycoprotein N-glycans in the form of hierarchical grammatical rules. Glycans can then be represented as hierarchical trees of numbers, each number corresponding to a state out of the allowed states for the given rule.

| Rule No. | Dependent on Rule No. | Code | # of Locations | States per Location | Deterministic Description |
|---|---|---|---|---|---|
| 2 | none | core fucose | 1 | 2 | to 1st GlcNAc of core can be attached Fucose at 6 positions, or nothing |
| 3 | none | man or ant | 2 | 3 | To each of two external 'core' mannose, can be attached antennae (GlcNAc), Mannose or nothing. |
| 4 | 3 | Multi-mannose extensions and limit | 3 | 2 | To 'top' mannose may be attached two 'strings' of up to 3 mannoses, connected in known positions. To 'bottom' mannose only one 'string' may be attached. |
| 5 | 3 | Antenna locations | 2 | 2 | If antennas (GlcNAc) start from the 'core' mannose, there are either 1 or 2, with fixed positions at each mannose: 2 and 4 on 'top', 2 and 6 on 'bottom'. |
| 6 | 3 | Bisecting GlcNAc | 1 | 2 | if both mannoses connect to antennas, then a GlcNAc may connect to position 4 of the 'back' mannose in the 'core'. |
| 7 | 3 | Antenna unit | up to 4 | 3 | the antenna GlcNAc is connected at position 4 to Gal, GalNAc, or to nothing (terminal) |
| 8 | 3 | Antenna extension/ termination | up to 4 | 5 | The antenna unit's Gal may be extended by one of the following: Nothing, Sialic acid at position 3 or 6, Gal at position 3, GlcNAc at position 3. All except the last option terminate the antenna. |
| 9 | 8 | Antenna length limit | up to 4 | 1 | No more than 2 antenna length units were observed for mammals. Therefore max antenna length counting from the 'core' is 5 sugars. |
| 10 | 7, 8? | Side Fucose or Lewis | up to 8? | 3 | If the 2-sugar unit is complete, the GlcNAc may be connected also to a fucose on position 3 or 4. If there is a terminal sialic acid, this is known as the Lewis 4-sugar. No more than ? Side fucoses are allowed per glycan. |

TABLE 3

Relative affinities of lectins to N-glycan subunits according to literature. This table has been used to construct a working model to predict array reactions such as the fingerprint assay, using vector multiplication as shown in equation (4) in the text.

| Subunit ID | con A | DBA | PNA | SBA | UEA-I | WGA |
|---|---|---|---|---|---|---|
| N0 | 0 | 0 | 0 | 0 | 0 | 10 |
| N1 | 30 | 0 | 0 | 0 | 0 | 0 |
| N2 | 0 | 0 | 10 | 0 | 0 | 0 |
| N3 | 0 | 0 | 0 | 0 | 20 | 0 |
| N4 | 0 | 0 | 0 | 0 | 0 | 0 |
| N5 | 0 | 0 | 0 | 0 | 0 | 50 |
| N6 | 0 | 0 | 0 | 0 | 0 | 50 |
| N15 | 10 | 0 | 0 | 0 | 0 | 10 |
| N16 | 10 | 0 | 0 | 0 | 0 | 10 |
| N17 | 0 | 0 | 0 | 0 | 0 | 0 |
| N7 | 0 | 0 | 0 | 0 | 0 | 0 |
| N8 | 80 | 0 | 0 | 0 | 0 | 0 |
| N9 | 20 | 0 | 0 | 0 | 0 | 0 |
| N10 | 0 | 0 | 0 | 0 | 0 | 10 |
| N11 | 0 | 0 | 0 | 0 | 0 | 10 |
| N12 | 0 | 0 | 0 | 0 | 0 | 10 |
| N13 | 0 | 0 | 0 | 0 | 50 | 0 |
| N14 | 0 | 0 | 0 | 0 | 0 | 0 |
| N18 | 0 | 0 | 0 | 0 | 0 | 0 |
| N19 | 0 | 0 | 0 | 0 | 0 | 0 |
| N20 | 0 | 0 | 0 | 0 | 0 | 0 |

TABLE 4

Sample use of 'Searcher' algorithm (stage 4) to interpret
results and find most likely combination.
Simulated results of subunit abundances (based on literature
data for whole glycans) for coagulation factor X were
combined with additional constraint rules, and fed to a linear
programming search for the most likely glycan combination.
These are compared with the original literature data

| Glycans | 1 | 2 | 3 | 4 | 5 | 6 | 7 | 8 | 9 | 10 | 11 | 12 | foreign |
|---|---|---|---|---|---|---|---|---|---|---|---|---|---|
| Rule 1 |  | 0.192 |  | 0.104 |  |  |  | 0.255 | 0.27 |  |  |  | 0.177 |
| Rule 2 | 0.062 | 0.249 |  |  |  |  | 0.093 | 0.189 | 0.154 |  | 0.116 | 0.110 | 0.0239 |
| Rule 3 |  | 0.156 |  |  | 0.091 |  |  | 0.280 | 0.114 |  | 0.176 | 0.106 | 0.124 |
| Rule 4 |  | 0.089 |  |  | 0.093 | 0.129 |  | 0.349 | 0.048 | 0.063 | 0.116 | 0.110 |  |
| Rule 5 | 0.063 | 0.129 | 0.026 |  | 0.093 |  |  | 0.308 | 0.178 |  | 0.116 | 0.084 |  |
| Rule 6 | 0.063 | 0.192 | 0.057 |  |  |  | 0.093 | 0.246 | 0.178 |  | 0.173 | 0.053 |  |
| Rule 7 | 0.063 | 0.129 | 0.026 |  | 0.093 |  |  | 0.308 | 0.178 |  | 0.116 | 0.084 |  |
| Lit. | 0.0205 | 0.138 | 0.0265 | 0.034 | 0.041 | 0.053 | 0.053 | 0.3005 | 0.125 | 0.043 | 0.082 | 0.084 |  |

Rule 1: [Subunits abundances];
Rule 2: [Rule 1] AND [biantennary glycans percentage, triantennary glycans percentage, tetraantennary glycans percentage, sialilated glycans percentage, glycans with root fucose percentage];
Rule 3: [Rule 2] AND [tetraantennary glycans don't contain root fucose];
Rule 4: [Rule 3] AND [glycans don't contain terminal HSO3 or unknown terminals];
Rule 5: [Rule 4] AND [glycan contain not more than one sialic bound];
Rule 6: [Rule 5] AND [number of antennas in glycan $\geq 2$ and $\leq 4$];
Rule 7: [Rule 6] AND [if glycan is triantennary and with root fucose then it has no split2, 4].

What is claimed is:

1. A method for analyzing a fingerprint for a carbohydrate polymer, the fingerprint featuring a plurality of addresses, each address containing a numeric value related to binding of a saccharide-binding agent to the carbohydrate polymer, the method comprising:
connecting a first address to at least one other address of the fingerprint to form a map;
if said first address is consistent with said at least one other address, determining said map to be internally consistent; and
repeating said connecting and determining at least once to form at least one additional map;
comparing said map to said at least one additional map to determine if said maps are mutually consistent; and
eliminating any mutually inconsistent maps.

2. The method of claim 1, further comprising:
receiving experimental data from a second assay;
converting said experimental data to form a second fingerprint;
performing said connecting and determining with said second fingerprint to form a second fingerprint map;
comparing said map to said second fingerprint map to determine if said maps are mutually consistent; and
eliminating any mutually inconsistent maps.

3. The method of claim 2, wherein converting said experimental data to form a second fingerprint further comprises:
analyzing a format of said experimental data;
if said format is not a numerical value format, converting said experimental data to at least one numerical value; and
creating said second fingerprint from said at least one numerical value.

4. The method of claim 2, wherein said experimental data for said second assay is obtained by contacting the saccharide-binding agent to a known carbohydrate polymer having at least one of a known function, a known sequence or a combination thereof.

5. The method of claim 4, wherein said second assay is performed under identical experimental conditions as for the carbohydrate polymer.

6. The method of claim 2, wherein said second assay is performed on specific carbohydrate polymer material for the carbohydrate polymer, said specific carbohydrate polymer material being identical as for binding the saccharide-binding agent to the carbohydrate polymer.

7. The method of claim 1, wherein the fingerprint is constructed according to data obtained from detecting binding of a saccharide-binding agent to the carbohydrate polymer.

8. The method of claim 1, wherein said data is obtained by:
detecting whether binding of said saccharide-binding agent to the carbohydrate polymer occurred as raw data;
converting said raw data to a numeric value; and
placing said numeric value as an address of the fingerprint to form the fingerprint.

9. The method of claim 8, wherein said saccharide-binding agent has an attached label and obtaining said raw data is performed by detecting a signal from said label, such that said raw data is formed by measuring said signal.

10. The method of claim 9, wherein converting said raw data is performed such that said numeric value is binary.

11. The method of claim 9, wherein converting said raw data is performed such that said numeric value is at least semi-quantitative.

12. The method of claim 8, wherein said experimental assay includes an immobilized saccharide-binding agent, such that obtaining said raw data further comprises:
incubating the carbohydrate polymer with said immobilized saccharide-binding agent to form a complex if the carbohydrate polymer binds specifically to said immobilized saccharide-binding agent; and
incubating said complex with a solubilized saccharide-binding agent for detecting a presence of said complex.

13. A method for integrating external data to a fingerprint for a sample carbohydrate polymer, the fingerprint featuring a plurality of addresses, each address containing a numeric value related to binding of a saccharide-binding agent to the sample carbohydrate polymer, the method comprising:

converting the external data to form an external fingerprint, the external data including at least one assay being performed on a carbohydrate polymer;

comparing said external fingerprint to the fingerprint for the sample carbohydrate polymer; and determining if said external fingerprint is consistent with the fingerprint for the sample carbohydrate polymer.

14. The method of claim 13, wherein converting the external data to form an external fingerprint further comprises:

analyzing a format of the external data;

if said format is not a numerical value format, converting the external data to at least one numerical value; and creating said external fingerprint from said at least one numerical value.

15. The method of claim 14, wherein alternatively if said format is a numerical value format, creating said external fingerprint from the external data directly.

16. A method for comparing a plurality of fingerprints for at least a first and a second carbohydrate polymer, each fingerprint featuring a plurality of addresses, each address featuring a numeric value related to binding of a saccharide-binding agent to the carbohydrate polymer, the method comprising:

comparing the numeric value for at least one address of the fingerprint for the first carbohydrate polymer to the numeric value for the corresponding address of the fingerprint for the second carbohydrate polymer; and determining similarity between the first and second carbohydrate polymers according to the comparison between the numeric values for the addresses.

17. The method of claim 16, wherein determining said similarity is performed according to a function for determining a degree of similarity between the fingerprint of the first and second carbohydrate polymers.

18. The method of claim 17, wherein said function provides a qualitative measurement of said degree of similarity.

19. The method of claim 17, wherein said function provides a quantitative measurement of said degree of similarity.

20. A method for searching through a database of fingerprint data with a fingerprint of a sample carbohydrate polymer, the database containing fingerprint data for a plurality of comparison carbohydrate polymers, the method comprising:

constructing the database according to an addressing system, the addressing system being at least partially obtained from fingerprint data for the plurality of comparison carbohydrate polymers;

converting the fingerprint of the sample carbohydrate polymer to a key;

searching through said addressing system with said key; and retrieving fingerprint data from at least one comparison carbohydrate polymer.

21. The method of claim 20, wherein constructing the database is performed such that the database features a plurality of records, each record including at least fingerprint data about a comparison carbohydrate polymer.

22. The method of claim 21, wherein interpretive information for interpreting said fingerprint data is also stored in said record.

23. The method of claim 22, wherein said interpretive information is a numeric value for assigning a probability to said fingerprint data.

24. The method of claim 22, wherein said interpretive information is a function for adjusting said fingerprint data.

25. The method of claim 20, wherein said key is formed of a plurality of addresses of the fingerprint as a linear sequence.

26. The method of claim 25, wherein each address is determined according to coordinates of a multi-dimensional array when constructing the database, such that when searching through said addressing system, said coordinates are determined from said linear sequence to locate at least one matching address.

27. The method of claim 20, wherein said key is formed of a plurality of segments, each segment featuring at least one address of the fingerprint.

28. The method of claim 20, wherein the database is constructed as a relational database, such that when searching through said addressing system, at least a portion of said relational database is accessed according to each segment.

29. A method for internally analyzing a fingerprint for extending fingerprint data for a carbohydrate polymer, the fingerprint featuring a plurality of addresses, each address containing a numeric value related to binding of a saccharide-binding agent to the carbohydrate polymer, the method comprising:

connecting a first address to at least one other address of the fingerprint to form a pattern;

if a value for said first address does not contradict a value for said at least one other address, determining said pattern to be internally coherent; and adding each internally coherent pattern to the fingerprint as extended fingerprint data.

* * * * *